(12) United States Patent
Kumaki et al.

(10) Patent No.: US 12,207,898 B2
(45) Date of Patent: Jan. 28, 2025

(54) EVALUATION TEST APPARATUS

(71) Applicant: NATIONAL UNIVERSITY CORPORATION YAMAGATA UNIVERSITY, Yamagata (JP)

(72) Inventors: Daisuke Kumaki, Yonezawa (JP); Shizuo Tokito, Yonezawa (JP)

(73) Assignee: NATIONAL UNIVERSITY CORPORATION YAMAGATA UNIVERSITY, Yamagata (JP)

(*) Notice: Subject to any disclaimer, the term of this patent is extended or adjusted under 35 U.S.C. 154(b) by 553 days.

(21) Appl. No.: 17/667,679

(22) Filed: Feb. 9, 2022

(65) Prior Publication Data

US 2022/0265146 A1 Aug. 25, 2022

Related U.S. Application Data

(63) Continuation of application No. PCT/JP2020/040914, filed on Oct. 30, 2020.

(30) Foreign Application Priority Data

Oct. 31, 2019 (JP) ................................ 2019-198883

(51) Int. Cl.
*A61B 5/00* (2006.01)
*A61B 5/0205* (2006.01)
*A61B 5/113* (2006.01)

(52) U.S. Cl.
CPC .......... *A61B 5/0053* (2013.01); *A61B 5/0205* (2013.01); *A61B 5/113* (2013.01);
(Continued)

(58) Field of Classification Search
CPC ..... A61B 5/0053; A61B 5/0205; A61B 5/113; A61B 5/4818; A61B 5/6891;
(Continued)

(56) References Cited

U.S. PATENT DOCUMENTS 6,176,117 B1 * 1/2001 Chen ....................... G01L 25/00
73/1.15

FOREIGN PATENT DOCUMENTS

CN 203328699 U 12/2013
CN 109475324 A 3/2019
(Continued)

OTHER PUBLICATIONS

Translation of JP-2017125737-A (Year: 2017).*
(Continued)

*Primary Examiner* — Nathaniel T Woodward
(74) *Attorney, Agent, or Firm* — BACON&THOMAS,PLLC

(57) ABSTRACT

An evaluation test apparatus is configured to evaluate or test measurement precision of a biological information measurement device configured to measure biological information. The evaluation test apparatus includes: a function generator configured to generate a plurality of input waveform signals by a predetermined operation; an indenter configured to pressure a piezoelectric element of the biological information measurement device; a vibration driver selected from a motor and a solenoid and configured to vibrate the indenter; and a control board configured to control the vibration driver. The control board includes an adder configured to combine the plurality of input waveform signals generated by the function generator. The vibration driver vibrates the indenter based on a composite waveform signal combined by the adder.

8 Claims, 5 Drawing Sheets

(52) U.S. Cl.
CPC .......... *A61B 5/4818* (2013.01); *A61B 5/6891* (2013.01); *A61B 2560/02* (2013.01)

(58) Field of Classification Search
CPC . A61B 2560/02; A61B 5/7221; A61B 5/4803; G01R 35/005; G01R 31/2839
USPC .......................................................... 73/1.01
See application file for complete search history.

(56) References Cited

FOREIGN PATENT DOCUMENTS

| | | | |
|---|---|---|---|
| JP | S63-3321 | A | 1/1988 |
| JP | H02-59638 | A | 2/1990 |
| JP | 2010-151772 | A | 7/2010 |
| JP | 2016-32501 | A | 3/2016 |
| JP | 2017125737 | A * | 7/2017 |
| JP | 2018-9926 | A | 1/2018 |

OTHER PUBLICATIONS

Office Action received in corresponding CN Appln. No. 2020800579234 with English translation.
International Search Report & Written Opinion cited in Japanese Appln. No. PCT/JP2020/040914 dated Dec. 15, 2020.

* cited by examiner

EVALUATION TEST APPARATUS

CROSS-REFERENCE TO RELATED APPLICATIONS

The present application is a continuation application of PCT international application No. PCT/JP2020/40914 filed on Oct. 30, 2020 which claims priority from Japanese Patent Application No. 2019-198883 filed on Oct. 31, 2019, and the entire contents of which are hereby incorporated by reference.

BACKGROUND

1. Technical Field

The present invention relates to an evaluation test apparatus configured to evaluate or test the measurement precision of a measurement device by generating a vibration, and more specifically to an evaluation test apparatus configured to evaluate or test the measurement precision of a biological information measurement device configured to measure biological information.

2. Related Art

Conventionally, there has been known a vibration test apparatus configured to inspect and test a subject by moving a piston up and down to vibrate the subject at a predetermined displacement, speed or acceleration waveform, which is disclosed, for example, in Japanese patent application Laid-Open No. 2010-151772. The entire contents of the disclosure are hereby incorporated by reference.

SUMMARY

An evaluation test apparatus according to the invention is configured to evaluate or test measurement precision of a biological information measurement device configured to measure biological information. The evaluation test apparatus includes: a function generator configured to generate a plurality of input waveform signals by a predetermined operation; an indenter configured to pressure a piezoelectric element of the biological information measurement device; a vibration driver selected from a motor and a solenoid and configured to vibrate the indenter; and a control board configured to control the vibration driver. The control board includes an adder configured to combine the plurality of input waveform signals generated by the function generator. The vibration driver vibrates the indenter based on a composite waveform signal combined by the adder.

DETAILED DESCRIPTION

Figure 1:
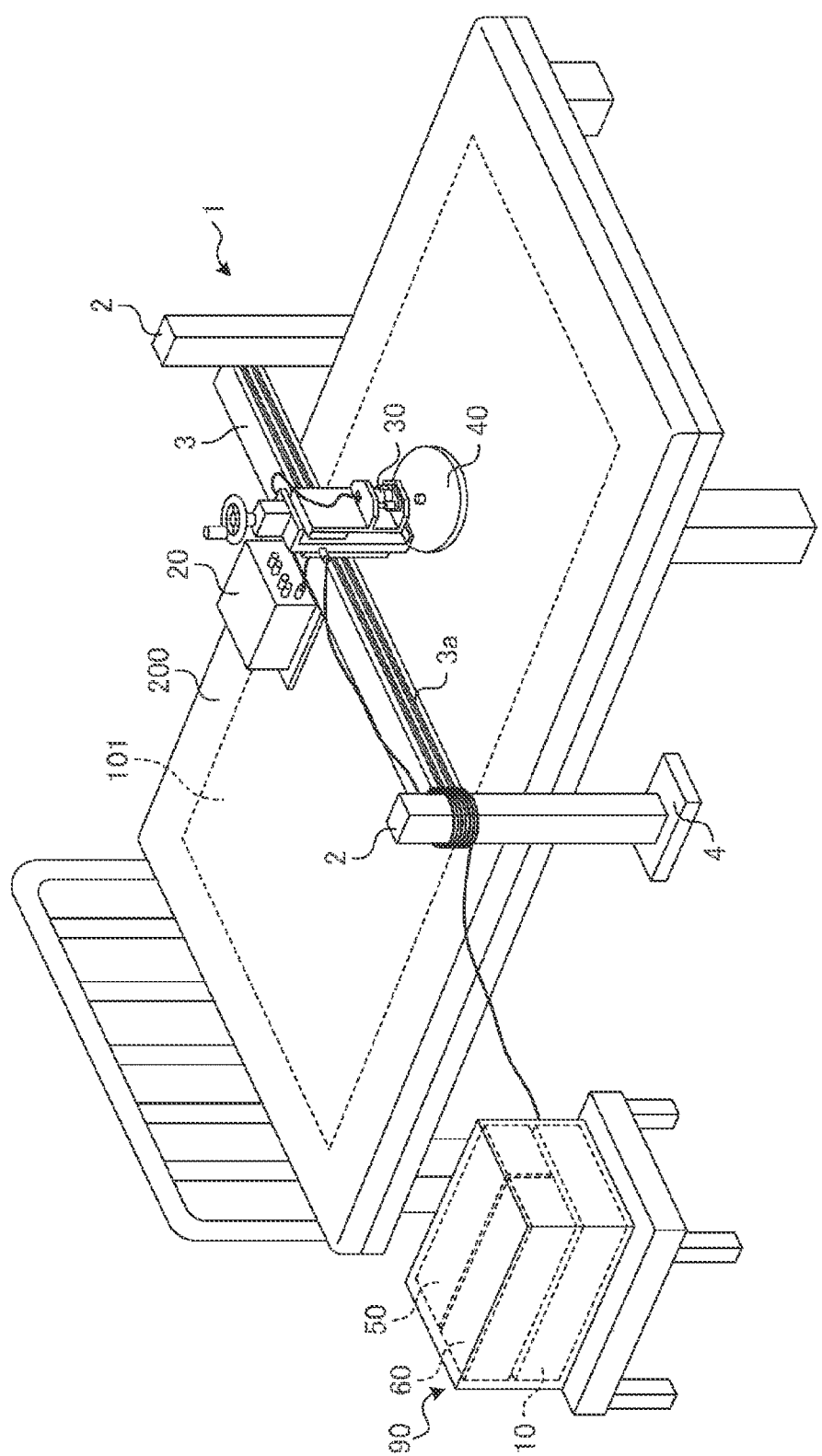
FIG. 1 is a perspective view illustrating a state where an evaluation test apparatus according to the invention is disposed on a bed.

In order to precisely test a subject by vibrating the subject, it is required to vibrate the subject at a frequency like that of the vibration actually generated. In particular, when a biological information measurement device configured to measure biological information of a living body (for example, the heartbeat and the breathing of a human body) is used as a subject, and the measurement precision of this biological information measurement device is evaluated or tested, it is difficult to precisely evaluate or test the measurement precision of the biological information measurement device because: the load of the vibration generated from an actual human is minute; the vibration has a plurality of frequencies of heartbeat, breathing, snoring and so forth; and a plurality of measurement states occur depending on the measuring position of the biological information measurement device. To solve the above-described problem, it is therefore an object of the invention to provide an evaluation test apparatus capable of precisely evaluate or test the measurement precision of a biological information measurement device configured to measure biological information.

Hereinafter, an embodiment of an evaluation test apparatus 1 according to the invention will be described with reference to FIG. 1 to FIG. 5.

With the present embodiment, as an example, the evaluation test apparatus 1 configured to evaluate or test the measurement precision of a bed biological information measurement device 100 will be described. The bed biological information measurement device 100 is configured to measure biological information such as the heartbeat, the breathing and the snoring of a subject (human body) lying down on a bed 200 and includes a bed sensor 101 as a vibration input unit which is put on the bed 200a.

<Configuration of Evaluation Test Apparatus 1>

Figure 2:
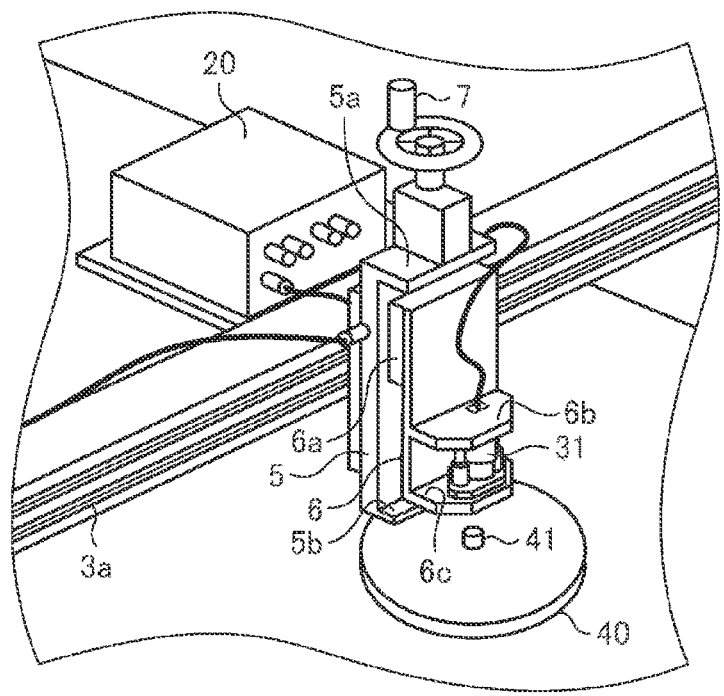
FIG. 2 is a perspective view illustrating enlarged essential parts of the evaluation test apparatus according to the invention.

FIG. 1 is a perspective view illustrating a state where the evaluation test apparatus 1 according to the invention is disposed on the bed 200. FIG. 2 is a perspective view illustrating enlarged essential parts of the evaluation test apparatus 1 according to the invention.

As illustrated in FIG. 1, the bed sensor 101 is put on bedclothing such as a mattress disposed on a bed plate of the bed 200. This bed sensor 101 is configured as a thin piezoelectric element to cover approximately the whole area of the bedclothing, but this is by no means limiting as long as the bed sensor 101 covers at least part of the bedclothing. For example, the bed sensor 101 may be put on only a region within which the bed sensor 101 can contact the upper part of a person lying down on the bed 200.

The evaluation test apparatus 1 includes a pair of vertical frames 2 disposed on the right side and the left side of the bed 200, and a horizontal frame 3 disposed above the bed 200. The horizontal frame 3 is coupled to the upper end sides of the pair of vertical frames 2 to form a portal frame extending across the bed 200.

Flat base plates 4 are coupled to the lower ends of the pair of vertical frames 2 to restrict the evaluation test apparatus 1 from moving. Here, the base plates 4 may have casters with stoppers to allow the evaluation test apparatus 1 to move in the longitudinal direction (front-to-back direction)

of the bed 200 before the bed biological information measurement device 100 is tested.

The horizontal frame 3 supports a controller 20 configured to control a vibration drive unit and a pressuring unit 30 including the vibration drive unit. In addition, a slide groove 3a is formed in the horizontal frame 3 in the lateral direction (right and left direction) of the bed 200.

Moreover, the evaluation test apparatus 1 includes an apparatus unit 90 in which a function generator 10 as an input waveform generator, an oscilloscope 50 as a waveform display, and a power supply BOX 60 configured to supply the controller 20 with power are built. Here, at least one of the function generator 10, the oscilloscope 50, and the power supply BOX 60 may not be built in the apparatus unit 90 but may be an individual component, or may be built in the controller 20.

As illustrated in FIG. 2, a back surface base 5 is provided on the back surface side of the controller 20, and a front surface base 6 and a handle 7 are attached to the back surface base 5.

The back surface base 5 includes a slider (not illustrated) formed on its surface facing the horizontal frame 3 and inserted in the slide groove 3a. The slide groove 3a and the slider allow the back surface base 5 to slide and move in the lateral direction (right and left direction) of the bed 200.

In addition, the back surface base 5 includes an upper end bending portion 5a formed at its upper end and bending to the front surface base 6. The back surface base 5 also includes a lower end bending portion 5b formed at its lower end and bending to the front surface base 6. The back surface base 5 is formed into approximately a U-shape in side view.

A voice coil motor 31 configured as the vibration drive unit is attached to the front surface base 6.

In addition, the front surface base 6 includes a stopper 6a extending from its surface to face the back surface base 5, an upper pedestal 6b configured to support the upper end of the voice coil motor 31, and a lower pedestal 6c configured to support the lower end of the voice coil motor 31.

The handle 7 includes a spiral screw between the back surface base 5 and the front surface base 6. By rotating the handle 7, the front surface base 6 can be moved up and down with respect to the back surface base 5 via the screw.

Here, when the handle 7 is rotated, the stopper 6a collides with the upper end bending portion 5a at an upper end limit value, and the stopper 6a collides with the lower end bending portion 5b at a lower end limit value. By this means, the moving range of the front surface base 6 with respect to the back surface base 5 in the up-and-down direction is defined.

The upper pedestal 6b includes a rectangular wire hole through which a wire to transmit an electrical signal from the function generator 10 to the controller 20 passes. In addition, as described above, the upper pedestal 6b supports the upper end of the voice coil motor 31 on its bottom surface.

The lower pedestal 6c supports the lower end of the voice coil motor 31, and includes a drive opening 6d (see FIGS. 4A and 4B) that allows a load cell 33 attached to the voice coil motor 31 to pass therethrough, as described later.

An indenter 40 configured to pressure the bed sensor 101 is put on the bed 200 below the lower pedestal 6c.

The bottom surface of the indenter 40 is formed of a circular plate, and includes a protrusion 41 formed on the center of the upper surface. The indenter 40 is not coupled to any part of the evaluation test apparatus 1, but can be freely detached from the evaluation test apparatus 1.

Moreover, it is preferred that the indenter 40 has a weight that allows the indenter 40 to sink in the bedclothing, and has a diameter of 10 to 30 cm and a weight of 1 to 5 kg as an example. The indenter 40 can be appropriately replaced with one having different size and weight, depending on the type of the biological information measurement device and the testing position.

<Block Diagram of the Evaluation Test Apparatus 1>

Figure 3:
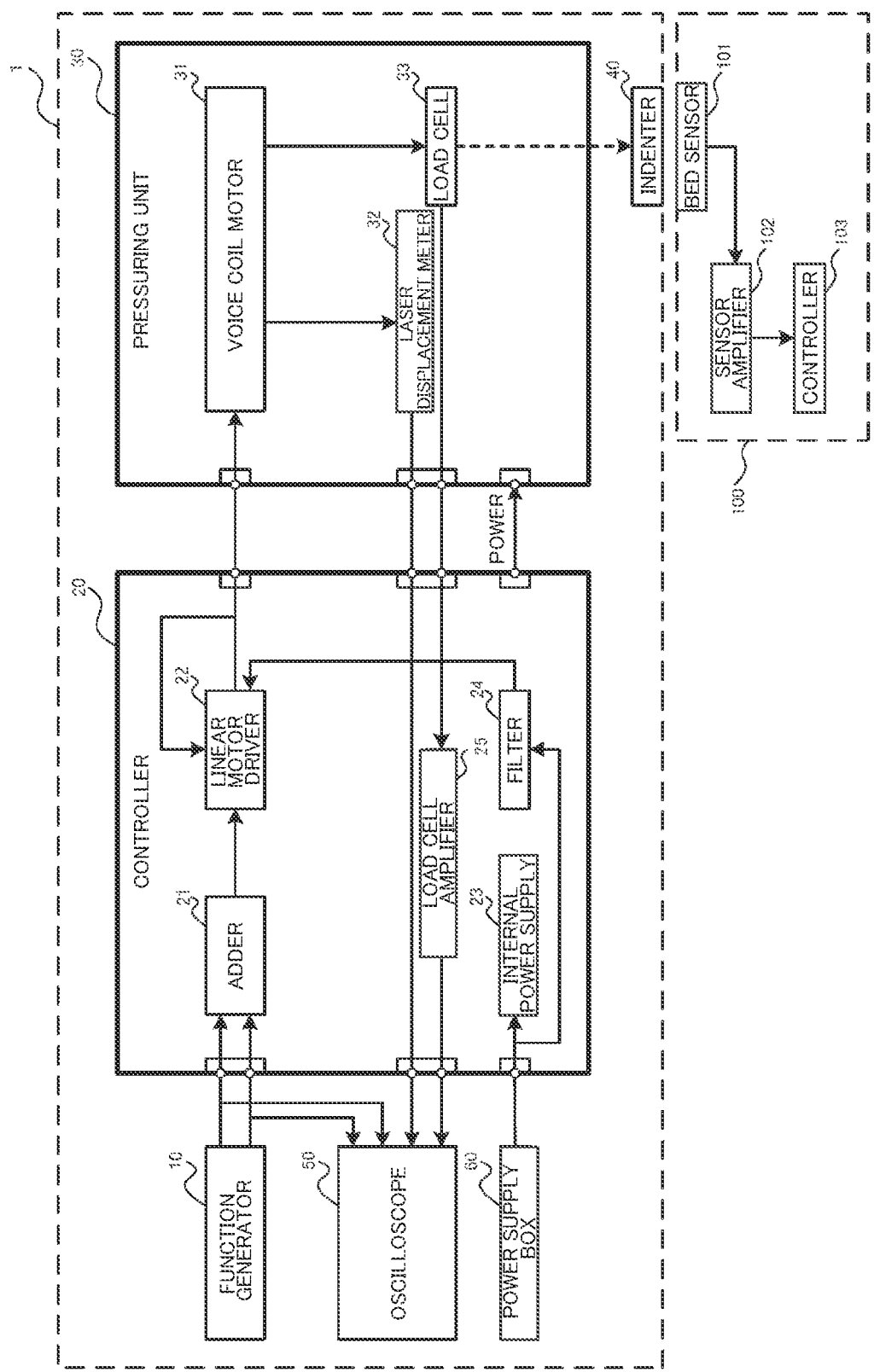
FIG. 3 is a block diagram illustrating the functional configuration of the evaluation test apparatus according to the invention.

Next, the functional configuration of the evaluation test apparatus 1 will be described with reference to FIG. 3. FIG. 3 is a block diagram illustrating the functional configuration of the evaluation test apparatus 1.

As illustrated in FIG. 3, the evaluation test apparatus 1 includes the function generator 10, the controller 20, the pressuring unit 30, the indenter 40, the oscilloscope 50, and the power supply BOX 60.

Here, with the present embodiment, the evaluation test apparatus 1 includes the oscilloscope 50, but the oscilloscope 50 is not necessarily essential to the evaluation test apparatus 1 according to the invention. The evaluation test apparatus 1 may not include the oscilloscope 50 but may output signals to a general-purpose oscilloscope provided outside.

The function generator 10 generates a plurality of input waveform signals indicating frequencies of arbitrary waveforms by a predetermined operation, and outputs the generated input waveform signals to the oscilloscope 50 and an adder 21 (described later) of the controller 20.

The controller 20 is a control board configured to control the pressuring unit 30, and at least includes the adder 21, a linear motor driver 22, an internal power supply 23, a filter 24, and a load cell amplifier 25.

The adder 21 is configured as a composite waveform generator to combine the plurality of input waveform signals outputted from the function generator 10, and output a combined input waveform signal as a composite waveform signal to the linear motor driver 22.

Here, with the present embodiment, although the function generator 10 generates two input waveform signals, and the adder 21 combines two input waveform signals, the number of input waveform signals is not limited to two as long as the number of input waveform signals is more than one.

The linear motor driver 22 receives the composite waveform signal outputted from the adder 21, and controls the amount of current to be outputted to the voice coil motor 31, based on the timing of the output, on the composite waveform signal. In addition, the linear motor driver 22 controls the voice coil motor 31 in real time while performing feedback control to feed back the amount of current outputted to the voice coil motor 31 to itself.

The internal power supply 23 receives power from the power supply BOX 60, and supplies the power to each of the elements of the controller 20.

The filter 24 receives power from the power supply BOX 60, filters noise, and supplies the power to the linear motor driver 22.

The load cell amplifier 25 receives a load signal from the load cell 33 described later, amplifies the inputted load signal, and outputs an amplified load signal to the oscilloscope 50.

The pressuring unit 30 includes the voice coil motor 31, a laser displacement meter 32, and the load cell 33.

The voice coil motor 31 is a motor including a coil bobbin as a mover 31a which linearly reciprocates in a magnetic field produced by a magnet.

Here, with the present embodiment, the voice coil motor 31 configured to linearly reciprocate is adopted as the vibration drive unit to vibrate the indenter 40, but a motor configured to rotationally reciprocate or a solenoid configured to linearly move may be adopted. Here, in order to provide pseudo vibration of biological information, it is preferable to adopt a voice coil motor (linear motor) which exhibits an excellent electrical response and allows precise and smooth control.

The load cell 33 is configured as a load detector to detect a force loaded on the indenter 40, and output a load signal indicating the detected force to the oscilloscope 50 via the load cell amplifier 25. The load cell 33 is coupled to the lower end of the mover 31a of the voice coil motor 31 (see FIG. 4).

The laser displacement meter 32 is configured as a displacement detector to detect the displacement of the vibration of the indenter 40 and output a displacement signal indicating the detected displacement to the oscilloscope 50. The laser displacement meter 32 is disposed on the front surface base 6 on the back surface side of the voice coil motor 31.

The indenter 40 is not coupled to the load cell 33, but the load cell 33 touches the indenter 40 by linearly reciprocating the voice coil motor 31.

The bed biological information measurement device 100 is configured to input the vibration of the indenter 40 from the bed sensor 101 to the controller 103 via a sensor amplifier 102.

The oscilloscope 50 receives the plurality of input waveform signals from the function generator 10, the displacement signal from the laser displacement meter 32, and the load signal from the load cell 33, and displays waveforms based on the plurality of input waveform signals and the displacement signal, and a load value based on the load signal. In addition, the oscilloscope 50 does not combine the plurality of input waveform signals but displays the waveforms based on the respective input waveform signals.

By this means, an examiner can compare the inputted input waveforms with the output waveforms actually outputted, and therefore to correct and feed back the input waveforms to be inputted. Moreover, the examiner can compare the output values and the output waveforms outputted by the bed biological information measurement device 100 with the load value and the waveforms displayed on the oscilloscope 50 of the evaluation test apparatus 1, and therefore can precisely correct and feed back the input waveforms. In particular, the oscilloscope 50 does not combine the plurality of input waveform signals but displays the waveforms based on the respective input waveform signals. This makes it easy to correct and feed back the input waveforms.

Here, with the present embodiment, the oscilloscope 50 does not combine the plurality of input waveform signals but displays the waveforms based on the respective input waveform signals. However, the oscilloscope 50 may combine the plurality of input waveform signals and display a composite waveform. Moreover, the oscilloscope 50 receives the plurality of input waveform signals from the function generator 10, but may receive a composite waveform signal combined by the adder 21 and display a waveform based on the composite waveform signal.

<Operation Mode of the Voice Coil Motor 33>

Figure 4A:
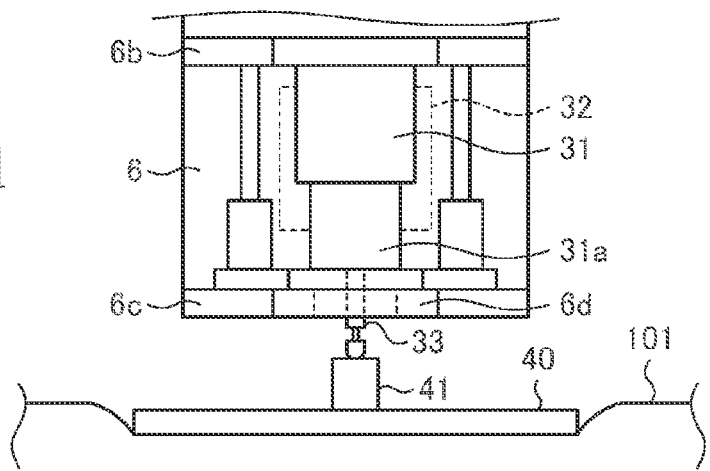
FIG. 4A is a conceptual diagram illustrating an operation mode of a voice coil motor of the evaluation test apparatus according to the invention.
Figure 4B:
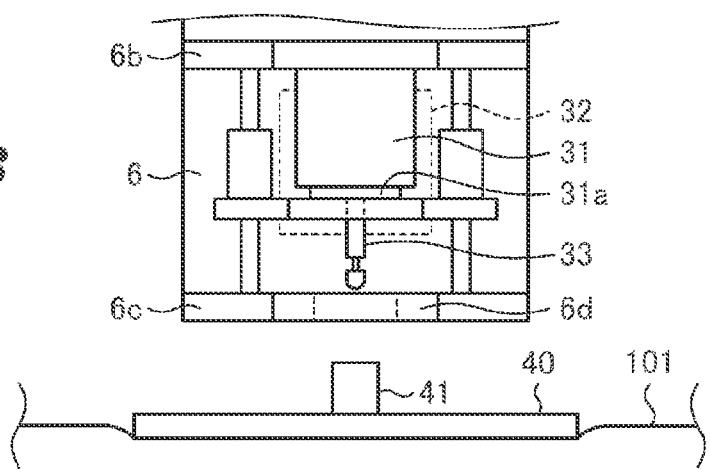
FIG. 4B is a conceptual diagram illustrating an operation mode of the voice coil motor of the evaluation test apparatus according to the invention.

Next, the operation modes of the voice coil motor 31 of the evaluation test apparatus 1 will be described with reference to FIGS. 4A and 4B. FIGS. 4A and 4B are conceptual diagrams illustrating the operation modes of the voice coil motor 31 of the evaluation test apparatus 1. Specifically, FIG. 4A is a conceptual diagram illustrating a pressurization operation mode where electricity is not applied to the voice coil motor 31, and the bed sensor 101 is pressured by the indenter 40, and FIG. 4B is a conceptual diagram illustrating non-pressurization operation mode where electricity is applied to the voice coil motor 31, and the bed sensor 101 is not pressured by the indenter 40.

As illustrated in FIGS. 4A and 4B, although the load cell 33 is coupled to the lower end of the mover 31a of the voice coil motor 31, the indenter 40 is coupled to neither the voice coil motor 31 nor the load cell 33.

As illustrated in FIG. 4A, when electricity is not applied to the voice coil motor 31, the mover 31a protrudes from a stator (main body) of the voice coil motor 31. The examiner rotates the handle 7 to lower the front surface base 6 to the position at which the load cell 33 coupled to the mover 31a touches the protrusion 41 of the indenter 40. It is possible to set the load of the pressure applied by the indenter 40 based on the degree of lowering the front surface base 6, that is, the amount of pushing the load cell 33 into the protrusion 41.

As illustrated in FIG. 4B, when electricity is applied to the voice coil motor 31, the mover 31a is retracted into the stator of the voice coil motor 31. When the mover 31a is retracted, the load cell 33 is apart from the protrusion 41 and is prevented from pressuring the indenter 40.

Then, the linear motor driver 22 causes a predetermined amount of current to be outputted (applied or not to be applied) to the voice coil motor 31, based on the composite waveform signal combined by the adder 21. By this means, the mover 31a linearly reciprocates to vibrate the indenter 40 at a frequency based on the composite waveform signal.

In particular, when the measurement precision of the bed biological information measurement device 100 including the bed sensor 101 put on bedclothing such as a mattress is evaluated or tested, it may be required to vibrate the indenter 40 at a high frequency. Then, when the indenter 40 is vibrated at a high frequency, the indenter 40 is bounced due to the repulsive force of the bedclothing and collides with the load cell 33. Consequently, it may not be possible to vibrate the indenter 40 at a proper frequency. With the present embodiment, the indenter 40 is coupled to neither the voice coil motor 31 nor the load cell 33, and therefore it is possible to prevent the indenter 40 bounced due to the repulsive force of the bedclothing from colliding with the load cell 33, and consequently to vibrate the indenter 40 at a proper frequency.

Moreover, the indenter 40 has a weight that allows the indenter 40 to sink in the bedclothing. Therefore, when the measurement precision of the bed biological information measurement device 100 including the bed sensor 101 is evaluated or tested, it is possible to vibrate the indenter 40 in the same way as the state where a person lies down on the bedclothing and the bed sensor 101 sinks.

Furthermore, the bottom surface of the indenter 40 is formed of a circular plate, and therefore the bed sensor 101 is not subjected to a vibration at a point, but is subjected to a vibration on a plane as if the heart of a human body vibrates.

<Operation Flow Until the Evaluation Test Apparatus 1 is Actuated>

Figure 5:
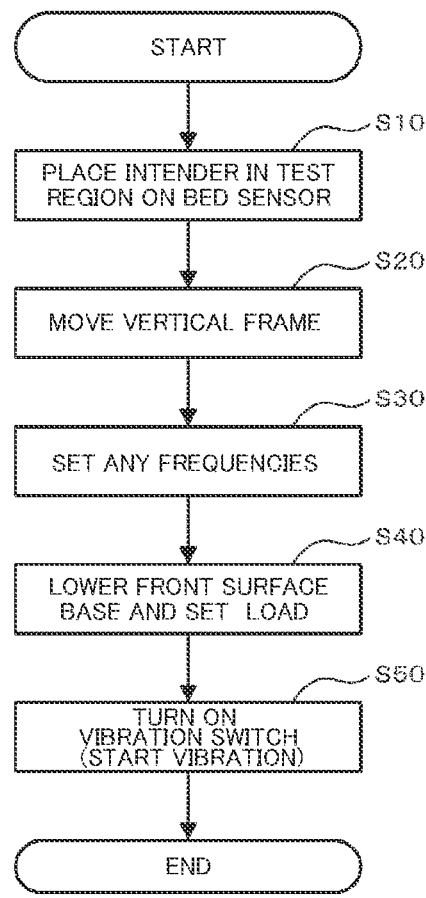
FIG. 5 is a flowchart illustrating an operation until the evaluation test apparatus according to the invention is actuated.

Next, an operation flow until the evaluation test apparatus 1 is actuated will be described with reference to FIG. 5. FIG. 5 is a flow chart illustrating an operation until the evaluation test apparatus 1 is actuated.

First, in step S10, the examiner disposes the indenter 40 in any test region on the bed sensor 101 where a test will be performed.

In step S20, the examiner moves the pair of vertical frames 2 to allow the load cell 33 to touch the protrusion 41 of the indenter 40.

That is, in the step 310 and the step 320, the examiner moves the evaluation test apparatus 1 to the test region of the bed sensor 101. Here, with the present embodiment, the step S20 is performed after the step 310, but may be performed before the step S10.

In step S30, the examiner operates the function generator 10 in a predetermined manner to set a plurality of frequencies which can be generated from a subject.

With the present embodiment, when the measurement precision of the bed biological information measurement device 100 is evaluated or tested, the examiner sets values for a frequency band of 1.0 to 10.0 Hz as the heartbeat of a human body, values for a frequency band equal to or lower than 1.0 Hz as the breathing, and values for a frequency band of 50.0 to 500 Hz as the snoring.

In step S40, the examiner rotates the handle 7 to lower the front surface base 6 to the position at which the load cell 33 coupled to the mover 31a touches the protrusion 41 of the indenter 40, and sets the load of the pressure applied by the indenter 40.

With the present embodiment, the load of the pressure applied to the bed sensor 101 is a value obtained by summing (1) the load of the pressure applied by the indenter 40 and (2) the weight of the indenter 40. Then, when the measurement precision of a biological information measurement device configured to measure the biological information of a human body as a subject is evaluated or tested, it is preferred to set a load equal to or lower than 1 N and close to zero to the load cell 33 to apply the load of the pressure to the protrusion 41 of the indenter 40, because the load of the vibration generated from an actual human is minute. That is, it is preferred that the load cell 33 does not press the protrusion 41 of the indenter 40 too much but touches the protrusion 41 of the indenter 40.

In addition, with the present embodiment, although the load applied to the indenter is set in the step S40 after the frequency is set in the step S30, the step 30 may be performed after the step S40.

Finally, in the step S50, the examiner turns on a vibration switch (not illustrated) of the evaluation test apparatus 1. By this means, the mover 31a of the voice coil motor 31 linearly reciprocates to vibrate the indenter 40 at the frequency based on the composite waveform signal.

As described above, according to the embodiment, the examiner assumes a plurality of input waveforms corresponding to the biological information such as heartbeat, breathing and snoring to be inputted to the bed sensor 101 of the bed biological information measurement device 100, taking into account the placement of the indenter 40 disposed on the bed sensor 101, and the evaluation test apparatus 1 generates signals of the assumed input waveforms and vibrates the indenter 40 based on a composite waveform signal obtained by combining the generated input waveform signals. Therefore, it is possible to precisely evaluate or test the measurement precision of the bed biological information measurement device 100.

In addition, with the evaluation test apparatus 1 according to the embodiment, the oscilloscope 50 receives the plurality of input waveform signals from the function generator 10, the displacement signal from the laser displacement meter 32, and the load signal from the load cell 33, and displays the waveforms based on the plurality of input waveform signals and the displacement signal, and the load value based on the load signal. Therefore, it is possible to compare the inputted input waveforms with the output waveforms actually outputted, and consequently to correct and feed back the input waveforms to be inputted.

Moreover, with the evaluation test apparatus 1 according to the embodiment, the indenter 40 is coupled to neither the voice coil motor 31 nor the load cell 33. Therefore, it is possible to prevent the indenter 40 bounced due to the repulsive force of the bedclothing from colliding with the load cell 33, and consequently to vibrate the indenter 40 at a proper frequency.

<Modification>

With the evaluation test apparatus 1 according to the embodiment, the indenter 40 is not coupled to any part of the evaluation test apparatus 1. However, the indenter 40 may be coupled to the load cell 33 or the mover 31a of the voice coil motor 31. In addition, the indenter 40 may not be coupled to the load cell 33, and the mover 31a of the voice coil motor 31, but may be supported by a support member which is neither the load cell 33 nor the voice coil motor 31. For example, a support member configured to support the indenter 40 to allow the indenter 40 to move up and down may be provided on the front surface base 6. In addition, with the embodiment, the evaluation test apparatus 1 includes the handle 7 attached to the back surface base 5 and rotated to allow the front surface base 6 to move up and down with respect to the back surface base 5. However, the evaluation test apparatus 1 may not include the handle 7, but the portal frame constituted by the vertical frames 2 and the horizontal frame 3 may be configured to move the horizontal frame 3 up and down with respect to the vertical frames 2.

Moreover, with the embodiment, the evaluation test apparatus 1 configured to evaluate or test the measurement precision of the bed biological information measurement device 100 including the bed sensor 101 has been described, but this is by no means limiting. The evaluation test apparatus may evaluate or test the measurement precision of a biological information measurement device including a piezoelectric element sensor provided on a seat part such as a cushion and a chair.

Furthermore, the evaluation test apparatus may evaluate or test the measurement precision of a biological information measurement device including a touch sensor attached to a part of a human body (for example, the arm and the head).

Furthermore, with the embodiment, the evaluation test apparatus configured to evaluate or test the measurement precision of the biological information measurement device configured to measure the biological information of a human body has been described, but this is by no means limiting. The evaluation test apparatus may evaluate or test the measurement precision of a biological information measurement device configured to measure the biological information of animals except for human (for example, a dog, a cat and a horse). According to the invention, the examiner assumes the plurality of input waveforms to be inputted to the biological information measurement device, taking into account the measurement state of the biological information measurement device, signals of the assumed input waveforms are generated, and the indenter is vibrated based on a composite waveform signal obtained by combining the generated input waveform signals. Therefore, it is possible to perform a precise simulation, and consequently to precisely evaluate or test the measurement precision of the biological information measurement device.

The invention claimed is:

1. An evaluation test apparatus configured to evaluate or test measurement precision of a biological information measurement device configured to measure biological information, the evaluation test apparatus comprising:

a function generator configured to generate a plurality of input waveform signals by a predetermined operation;

an indenter configured to pressure a piezoelectric element of the biological information measurement device;

a vibration driver selected from a motor and a solenoid and configured to vibrate the indenter; and a control board configured to control the vibration driver, the control board including an adder configured to combine the plurality of input waveform signals generated by the function generator, wherein the vibration driver vibrates the indenter based on a composite waveform signal combined by the adder.

2. The evaluation test apparatus according to claim 1, wherein the vibration driver causes the piezoelectric element via the indenter to generate a vibration of a load equal to or lower than 10 N at a frequency of 0 to 10000 Hz.

3. The evaluation test apparatus according to claim 1, wherein:

the biological information measurement device is a bed biological information measurement device configured to measure biological information which is at least one of movement, cardiac sound, heartbeat, breathing and snoring of a human body; and the piezoelectric element is put on a bed.

4. The evaluation test apparatus according to claim 1, further comprising:

a waveform display configured to display a waveform signal as a waveform; and a vibration waveform output device configured to output a vibration waveform signal of a vibration waveform of an actual vibration of the indenter, wherein:

the waveform display receives the vibration waveform signal outputted from the vibration waveform output device, and the plurality of input waveform signals generated by the function generator; and the waveform display displays a vibration waveform based on the vibration waveform signal and input waveforms based on the input waveform signals.

5. The evaluation test apparatus according to claim 4, wherein the vibration waveform output device includes:

a load cell configured to detect a force loaded on the indenter by the vibration driver; and a displacement meter configured to detect displacement of vibration of the indenter caused by the vibration driver, and wherein the vibration waveform output device outputs the load signal detected by the load cell and the displacement signal detected by the displacement meter to the waveform display.

6. The evaluation test apparatus according to claim 5, wherein:

the vibration driver and the load cell are coupled to one another;

the indenter is coupled to neither the vibration driver nor the load cell;

in a case of a pressurization operation, the vibration driver moves the load cell to the indenter to cause the load cell to touch the indenter, so that the piezoelectric element of the biological information measurement device is pressured by the indenter; and in a case of a non-pressurization operation, the vibration driver retracts the load cell from the indenter to space the load cell from the indenter, so that the piezoelectric element of the biological information measurement device is not pressured by the indenter.

7. The evaluation test apparatus according to claim 6, wherein:

a bottom surface of the indenter is formed of a circular plate; and a protrusion to touch the load cell is formed on a center of an upper surface of the indenter.

8. The evaluation test apparatus according to claim 6, wherein the indenter has a weight that allows the piezoelectric element of the biological information measurement device to sink when the indenter is put on the piezoelectric element.

* * * * *